(12) United States Patent
Kim et al.

(10) Patent No.: US 11,508,559 B2
(45) Date of Patent: Nov. 22, 2022

(54) PORTABLE PLASMA DEVICE

(71) Applicant: FEMTO SCIENCE INC, Hwaseong-si (KR)

(72) Inventors: Moo Hwan Kim, Hwaseong-si (KR); Yeon Sook Chang, Hwaseong-si (KR)

(73) Assignee: FEMTO SCIENCE INC, Hwaseong-si (KR)

( * ) Notice: Subject to any disclaimer, the term of this patent is extended or adjusted under 35 U.S.C. 154(b) by 671 days.

(21) Appl. No.: 16/541,686

(22) Filed: Aug. 15, 2019

(65) Prior Publication Data

US 2020/0083023 A1    Mar. 12, 2020

(30) Foreign Application Priority Data

Sep. 4, 2018   (KR) .................. 10-2018-0105196

(51) Int. Cl.
*H01J 37/32*   (2006.01)
*H05H 1/34*   (2006.01)
*H01J 37/34*   (2006.01)
*A61N 1/04*   (2006.01)

(52) U.S. Cl.
CPC .... *H01J 37/32532* (2013.01); *H01J 37/3488* (2013.01); *H05H 1/34* (2013.01); *A61N 1/0404* (2013.01)

(58) Field of Classification Search
None
See application file for complete search history.

(56) References Cited

U.S. PATENT DOCUMENTS

| 6,440,302 B1 * | 8/2002 | Leipziger | C02F 1/003 |
|---|---|---|---|
| | | | 210/473 |
| 2006/0200122 A1 | 9/2006 | Sartor et al. | |
| 2009/0125023 A1 | 5/2009 | Stephen et al. | |
| 2011/0183284 A1 | 7/2011 | Michizo et al. | |
| 2014/0234795 A1 | 8/2014 | Holbeche et al. | |
| 2016/0338184 A1 | 11/2016 | Holbeche | |

FOREIGN PATENT DOCUMENTS

| CN | 108451632 A | 8/2018 |
|---|---|---|
| JP | 2015160134 A | 9/2015 |
| KR | 20100107290 A | 10/2010 |
| KR | 10-1171091 B | 8/2012 |
| KR | 101 407 672 B1 | 6/2014 |
| KR | 10-1577207 B1 | 12/2015 |
| KR | 101 794 542 B1 | 11/2017 |
| KR | 101794542 * | 11/2017 |
| KR | 101 851 389 B1 | 4/2018 |
| KR | 10-2018-0057809 A | 5/2018 |

OTHER PUBLICATIONS

EP Application No. 19 191 512.3, Office Action dated Sep. 22, 2021, 6 pages.
Stoffels et al., "Plasma needle for in vivo medical treatment: recent developments and perspectives", Plasma Sources Science and Technology, Institute of Physics Publishing, vol. 15, No. 4, pp. S169-S180, Nov. 1, 2006 doi: 10.1088/0963-0252/15/4/S03.
European Search Report in related European Patent Application No. 19191512 dated Jan. 24, 2020 (10 pages).

* cited by examiner

*Primary Examiner* — Ashok Patel
(74) *Attorney, Agent, or Firm* — Lathrop GPM LLP

(57) ABSTRACT

The present disclosure relates to a portable plasma device which is convenient to carry and has excellent performance and is capable of simply, uniformly, and locally treating an inner surface of a microstructure such as a microwell plate by easily adjusting a plasma flame.

4 Claims, 8 Drawing Sheets

PORTABLE PLASMA DEVICE

CROSS-REFERENCE TO RELATED APPLICATION

This application claims priority to and the benefit of Korean Patent Application No. 10-2018-0105196, filed on Sep. 4, 2018, the disclosures of which are incorporated herein by reference in its entirety.

BACKGROUND

1. Field of the Invention

The present disclosure relates to a portable plasma device.

2. Discussion of Related Art

Plasma has been mainly utilized in the field of surface modification and coating of materials, environmental purification, and the like. Recently, research on the applicability to a biomedical field has been gradually expanded. Also, in recent years, research has been conducted to use low-temperature atmospheric plasma for the purpose of sterilization or pasteurization in a region of 50° C. or less. In most cases, an electrode structure of a tip of a low-temperature atmospheric-pressure plasma device is formed in a needle electrode structure having an acicular electrode shape and in various configurations and schemes depending on a power supply. In the above-described scheme, mainly, an inert gas is injected from the outside, and a high voltage is applied to the needle electrode structure to generate plasma.

Meanwhile, since conventional portable plasma devices are mainly developed for skin beauty, the intensity of plasma is weak, and the form of the conventional portable plasma device and the method of generating the plasma are not suitable for use in a biomedical field. In order to make active use of the plasma in the biomedical field, miniaturization and portability of the device and ease of control of the device are required. However, surface treatment plasma devices used in the conventional biomedical field have difficulty in adjusting the intensity of a plasma flame according to a user's intention, and it is not easy to uniformly and locally treat an inner surface of a microstructure, such as a microwell plate, due to the size of the device itself.

PRIOR-ART DOCUMENTS

Patent Documents (Patent Document 1) Korean Patent Application No. 10-1577207
(Patent Document 2) Korean Patent Application Publication No. 10-2018-0057809

SUMMARY OF THE INVENTION

The present disclosure is directed to a portable plasma device which is convenient to carry and has an excellent performance and is capable of simply, uniformly, and locally treating an inner surface of a microstructure such as a microwell plate by easily adjusting a plasma flame.

According to an aspect of the present disclosure, there is provided a portable plasma device comprising a housing, a push member positioned on one surface of the housing and installed to be movable downward in a longitudinal direction of the housing to control emission of a plasma flame, a holding member provided on a surface opposite to one surface on which the push member is installed, and a plasma emission part positioned on a lower portion of the housing.

BRIEF DESCRIPTION OF THE DRAWINGS

The above and other objects, features, and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
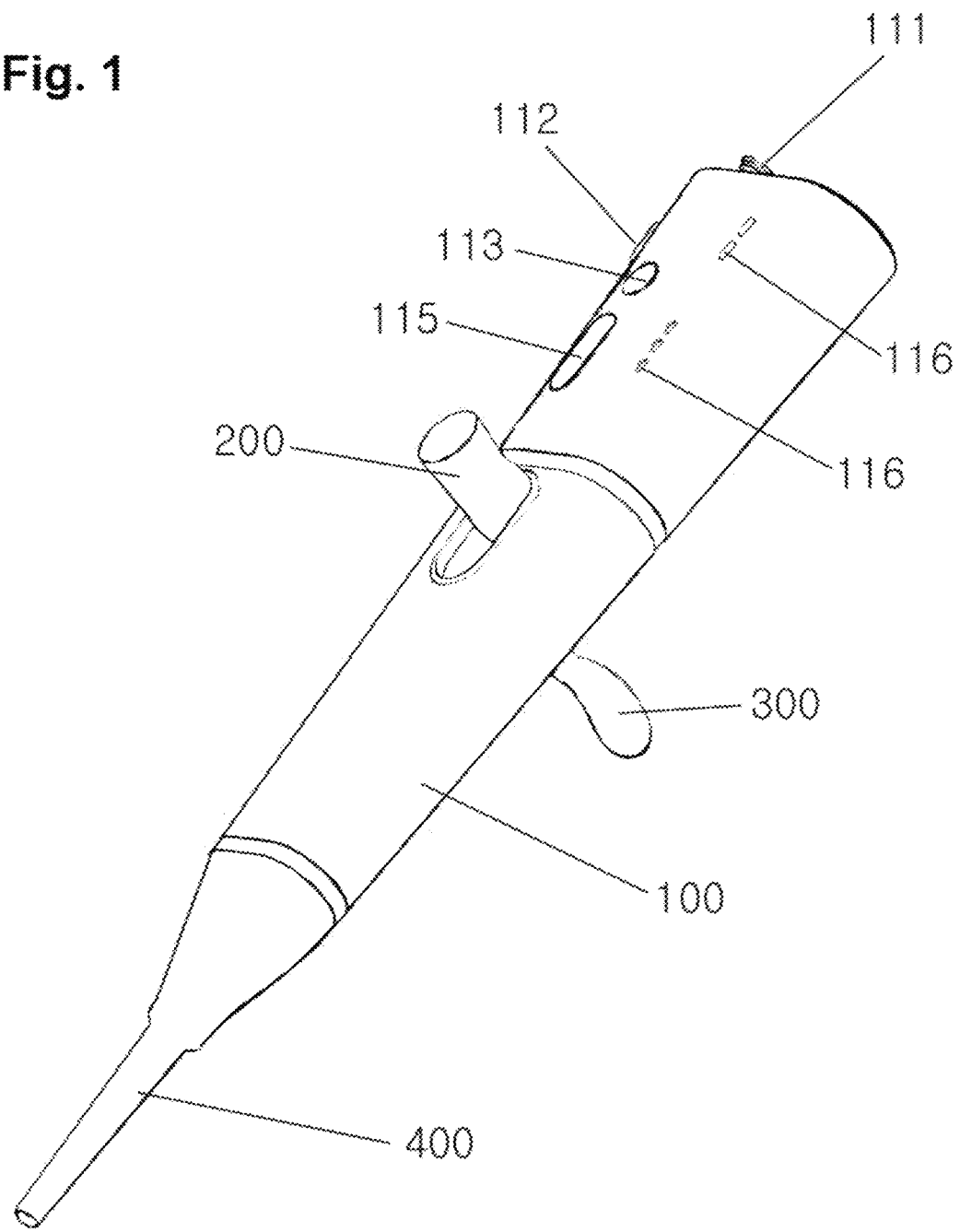
FIG. 1 is a perspective view of a portable plasma device according to a first embodiment.
Figure 2:
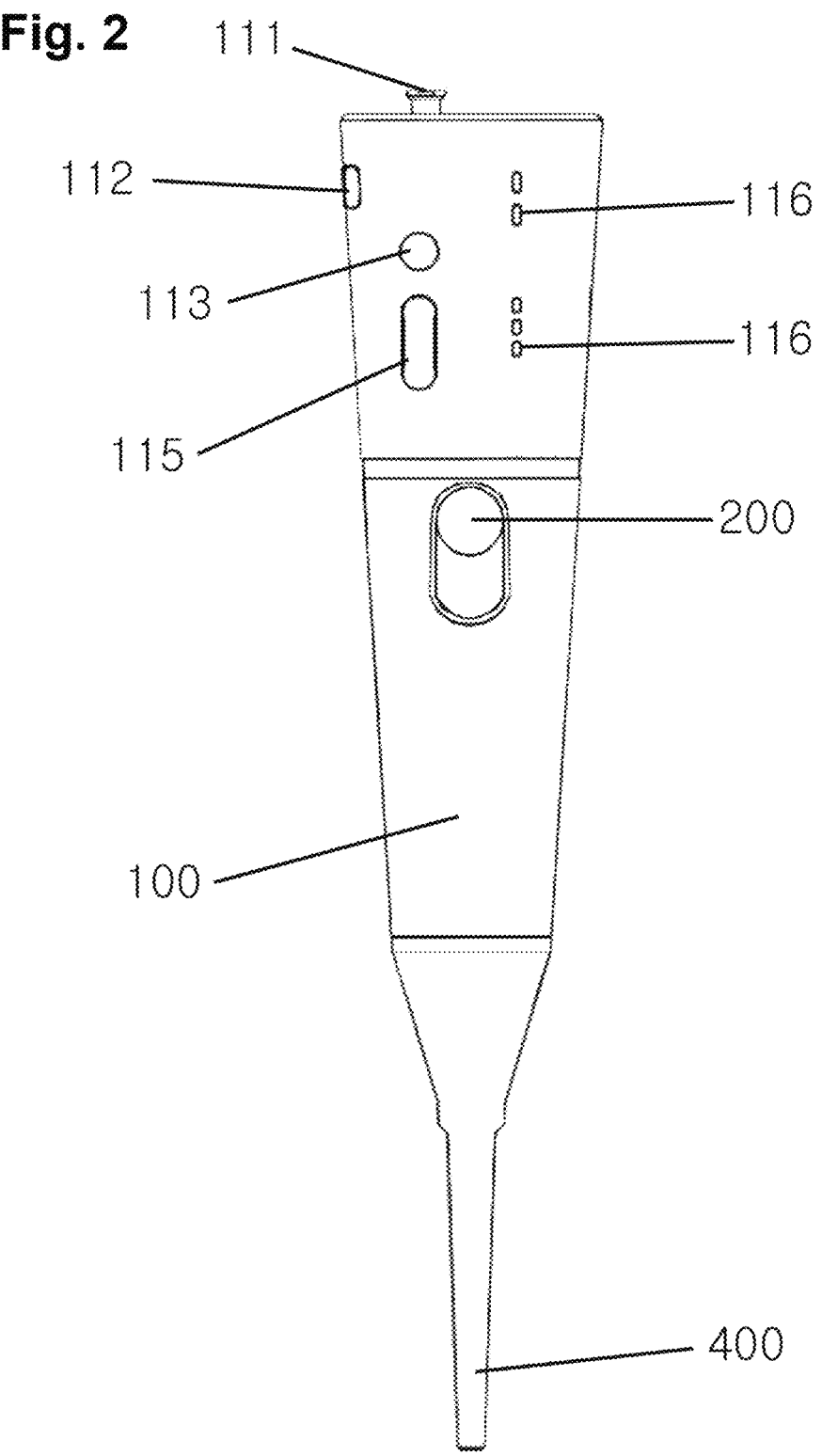
FIG. 2 is a front view of the portable plasma device according to the first embodiment.
Figure 3:
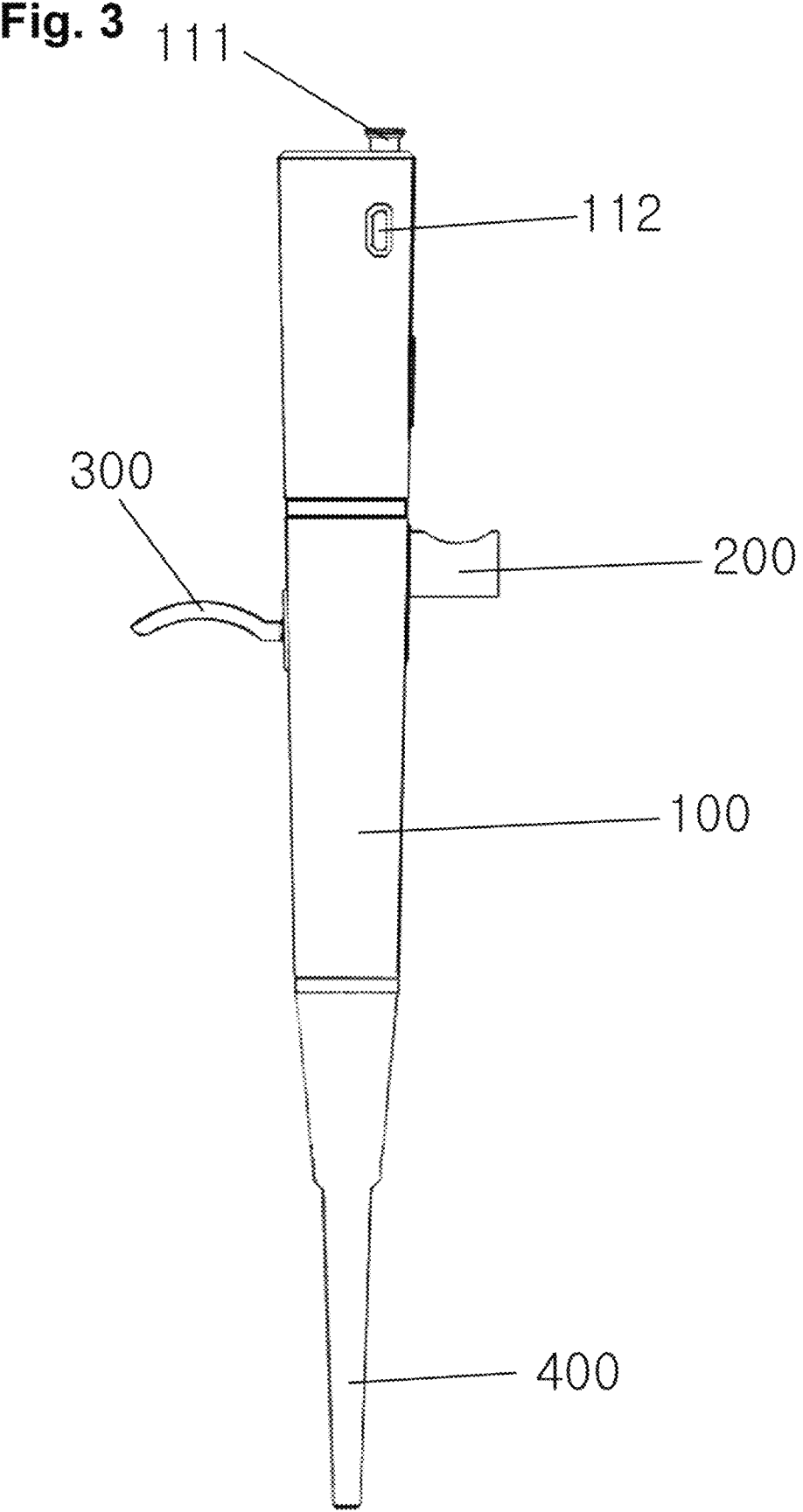
FIG. 3 is a side view of the portable plasma device according to the first embodiment.
Figure 4:
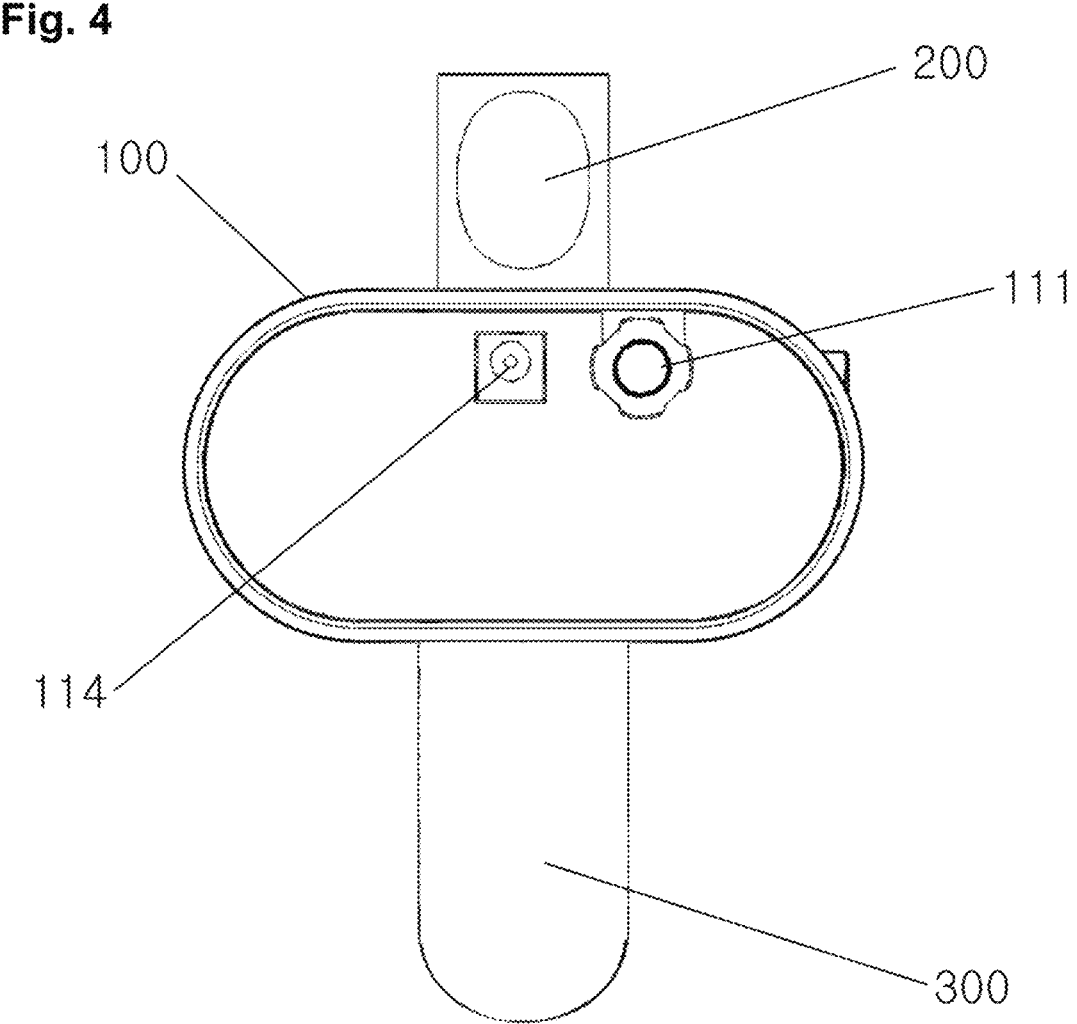
FIG. 4 is a top view of the portable plasma device according to the first embodiment.

Since the present disclosure may be modified to various forms and comprise various exemplary embodiments, specific exemplary embodiments will be illustrated in the drawings and described in detail. However, the description is not intended to limit the present disclosure to the specific exemplary embodiments, and it is to be understood that all the changes, equivalents, and substitutions belonging to the spirit and technical scope of the present disclosure are comprised in the present disclosure.

The terms such as "first," "second," "A," "B," etc. may be used to describe various components, but the components are not limited by the terms. These terms are used only to distinguish one component from another component. For example, a first component may be named a second component, and similarly, the second component may also be named the first component without departing from the scope of the present disclosure. The term "and/or" means any one or a combination of a plurality of related items.

It will be appreciated that terms such as "comprising", "having", etc. are intended to designate the presence of characteristics, numbers, steps, operations, components, parts, or combinations thereof, and do not exclude presence or addition of one or more other characteristics, numbers, steps, operations, components, parts, or a combination thereof.

Prior to describing drawings in detail, the division of configuration units in the present specification is only a division by the main function of each configuration unit. In other words, two or more of the configuration units to be described below may be combined into a single configuration unit, or one configuration unit may be divided into two or more units according to subdivided functions. Each of the configuration units to be described below may additionally perform a part or all of the functions among functions set for other configuration units other than being responsible for the main function, and some main functions taken by each of the configuration units may be exclusively taken and performed by other configuration units.

When a method or an operating method is performed, steps of the method may be performed in a different order from a described order unless a specific order is clearly mentioned in the context. In other words, steps may be performed in the same order as described, performed substantially simultaneously, or performed in reverse order.

FIGS. 1 to 4 are views illustrating a portable plasma device according to a first embodiment. Referring to FIGS. 1 to 4, the portable plasma device of the present disclosure comprises a housing 100, a push member 200 positioned on one surface of the housing 100 and installed to be movable downward in a longitudinal direction of the housing 100 to control the emission of a plasma flame, a holding member 300 provided on a surface opposite to one surface on which the push member is installed, and a plasma emission part 400 positioned on a lower portion of the housing 100.

The housing 100 has a hollow shape which extends in an axial direction and basically comprises an inner space and may be divided into a grip portion, an upper portion, and a lower portion. The "grip portion" is a portion of the housing 100 that a user grips by hand when the user uses the portable plasma device. The "upper portion" is a portion of the housing 100 that is positioned above the grip portion and is not gripped with respect to the grip portion when the user grips the grip portion of the portable plasma device by hand. The "lower portion" is a portion of the housing 100 that is positioned below the grip portion with respect to the grip portion when the user grips the grip portion of the portable plasma device by hand.

The push member 200 is provided on one surface of the housing 100 so as to be movable downward in the longitudinal direction of the housing 100 to control the emission of the plasma flame. With the above-described configuration, the portable plasma device of the present disclosure may emit the plasma flame through the plasma emission part 400 by a downward movement of the push member 200. The downward movement is adjusted by a downward force of a user's thumb on the push member 200 applied by the user while the user is gripping the housing 100. The push member 200 may further comprise an elastic member (not shown) configured to return the position of the push member 200, which is moved in response to the force applied downward, to the original position.

The holding member 300 is provided on the opposite surface of one surface on which the push member 200 is provided. The holding member 300 is brought into close contact with a partial surface of a user's index (or middle) finger so that the housing 100 may be stably gripped when the force is applied to the push member 200. As one specific example, the holding member 300 may have a curved shape so as to come into close contact with the partial surface of the user's index (or middle) finger.

By using the push member 200 and the holding member 300, the user may apply an appropriate force to the push member 200 to operate the plasma device. Thus, the emission of the plasma flame may be stably and easily controlled. In addition, the user may easily and freely operate an operating member such as a power button 113 or a setting button 115, which is provided on the upper portion of the housing 100, using only fingers of the hand which grips the housing 100 even when the user grips the housing 100 with one hand and grips a vial, a test tube, a well plate, or the like with the other hand.

Accordingly, the portable plasma device of the present disclosure allows the user to freely use the plasma device during the time required for operation without inappropriate stress applied to the thumb of the user, enabling the plasma device to operate accurately and repeatedly under the control of the user.

The housing 100 may comprise one or more of a gas inlet 111, a charging terminal 112, the power button 113, an external ground connection part 114, the setting button 115 configured to set an output intensity of the plasma flame, and a display part 116 configured to display a set and operating state.

The gas inlet 111 is a part configured to receive a gas required for plasma discharging from the outside and may be connected to a container, a tank, or the like which contains the gas. The connection may be performed using a hose, a tube, a pipe, or the like.

The charging terminal 112 may be connected to an external power source to charge a battery 121. The power button 113 may turn on/off the plasma device.

The external ground connection part 114 may be further comprised. The external ground connection part 114 may be connected to a ground line (not shown) to ground to an external metal plate (not shown). When the external ground connection part 114 and the external metal plate are connected to each other by the ground line, the emission intensity of the plasma flame may be increased, and thus the efficiency of modifying, coating, and sterilizing an inner surface of a vial, a test tube, a well plate, or the like may be increased. The external metal plate is made of a conductive material, and a plasma flame emission target such as a vial, a test tube, a well plate, or the like is placed between the external metal plate and the plasma emission part.

Further, the housing 100 may comprise the setting button 115 and the display part 116. The setting button 115 may set the output intensity of the plasma flame. The display part 116 may display information necessary for the operation of the plasma device, such as the remaining amount of the battery 121, in addition to displaying the set intensity.

The external power button 113, the setting button 115, and the display part 116 may be positioned on the upper portion of the housing 100. Thus, the user may easily and freely operate the power button 113 and the setting button 115 with the fingers of the hand which grips the housing 100 of the plasma device while gripping the housing 100 and clearly see signals of the display part 116 in response to the operation of the button.

Meanwhile, in the first embodiment according to the present disclosure, as shown in FIGS. 1 to 4, the lower portion of the housing 100, which is connected to the plasma emission part 400, may have a symmetrical shape with respect to a central axis of the longitudinal direction.

Figure 5:
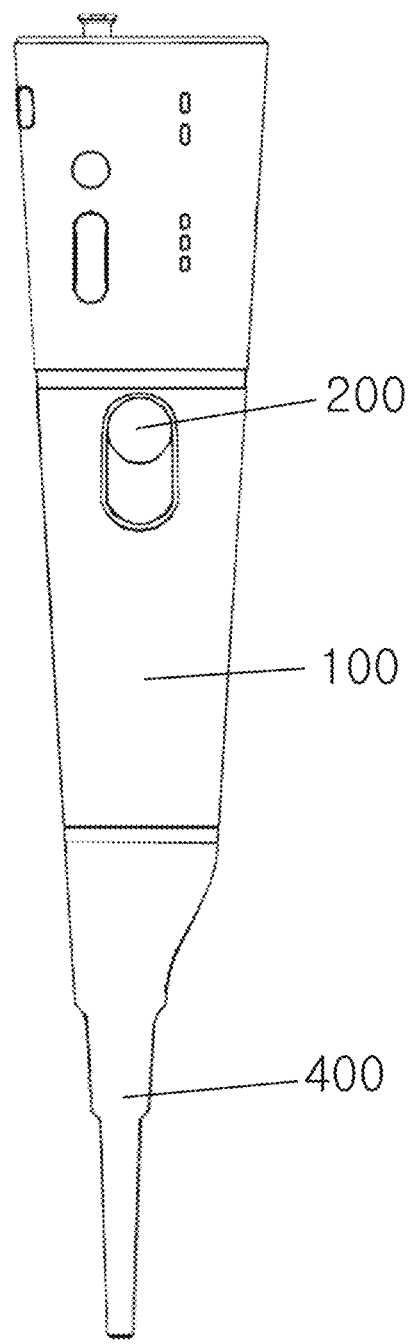
FIG. 5 is a front view of a portable plasma device according to a second embodiment.

In addition, in a second embodiment according to the present disclosure, as shown in FIG. 5, a plasma emission part 400 may be formed in an asymmetrical shape biased to one side with respect to a central axis of the housing in a longitudinal direction. When the plasma emission part 400 is positioned to be asymmetrically biased to one side, a user may easily grasp an emission state of a plasma flame while gripping and using a portable plasma device. In addition, when the user grips the portable plasma device with one hand and grips a vial, a test tube, or the like with the other hand, it is convenient to use the portable plasma device in a natural posture by tilting the portable plasma device. In addition, when putting the device after use, a separation distance from peripheral objects becomes long such that contamination of an electrode may be prevented.

Figure 6:
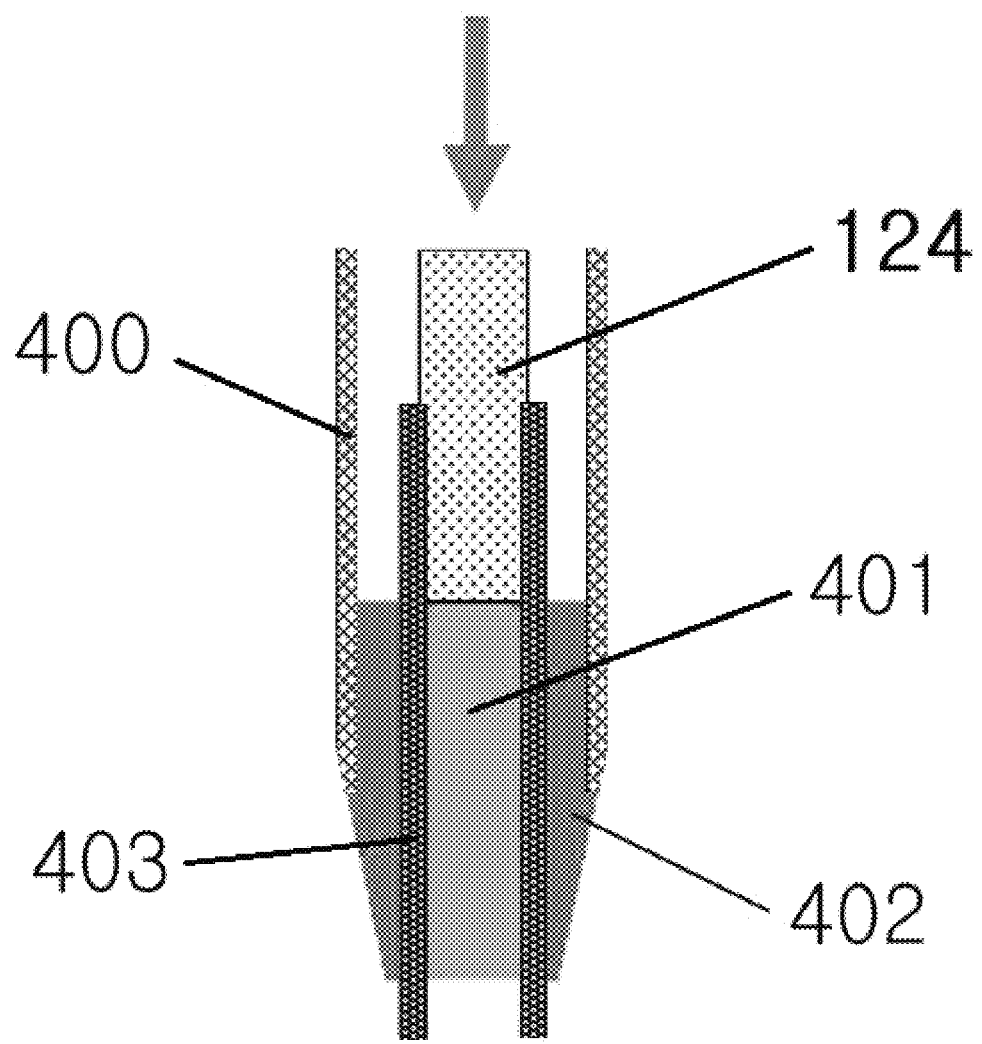
FIG. 6 is an enlarged view of a plasma emission part according to one embodiment.

As shown in FIG. 6, the plasma emission part 400 comprises an emission electrode 401, a ground electrode 402, and a dielectric wall 403 at an end portion thereof through which the plasma is emitted.

The emission electrode 401 may be made of a material such as, but not limited to, gold, platinum, silver, copper, moly-manganese, aluminum, stainless steel, or an alloy thereof, and may be made of various conductive metals. The emission electrode 401 may be supplied with the gas introduced through the gas inlet 111 by being connected to a gas tube 124. A plasma discharge is performed by applying a voltage to the gas supplied as described above to generate and emit the plasma flame. The emission electrode 401 may be in the shape of a hollow pipe or tube through which the gas may move into the electrode. The form of the emitted plasma flame may be controlled by adjusting the shape and inner hollow size of the emission electrode 401.

In a specific example, when the emission electrode 401 has a hollow pipe or tube shape, in order to generate the plasma flame suitable for treating an inner surface of a microstructure, such as a microwell plate, an inner diameter of the pipe or tube may be, but is not limited to being, in a range of 0.05 mm to 3.0 mm.

The ground electrode 402 may be disposed to be spaced apart from the emission electrode 401 so as to surround the periphery of the emission electrode 401. Like the emission electrode 401, the ground electrode 402 may be made of a material such as, but not limited to, gold, platinum, silver, copper, moly-manganese, aluminum, stainless steel, or an alloy thereof, and may be made of various conductive metals. The ground electrode 402 may also be formed of a plastic, acrylic, resin, ceramic-, or quartz-based material, and a surface of the plastic material may be coated with the above-described metallic material.

The dielectric wall 403 is positioned between the emission electrode 401 and the ground electrode 402 to prevent the emission electrode 401 and the ground electrode 402 from coming into direct contact with each other. The dielectric wall 403 may be made of a plastic-, acrylic-, resin-, ceramic-, or quartz-based material, and may be coated on at least one of the emission electrode 401 and the ground electrode 402.

The emission electrode 401 and the ground electrode 402 may operate due to such a configuration of the plasma emission part 400, thereby generating the plasma flame. The emitted plasma flame includes radicals and ions. The generated radicals and ions may modify, coat, or sterilize an inner surface of a microstructure, such as a microwell plate.

Meanwhile, when the external ground connection part 114 is connected to the external metal plate (external ground) by being connected to the ground line, the ground electrode 402 may not operate, and the emission electrode 401 and the external metal plate may interact with each other to discharge the plasma flame to a plasma treatment target placed between the emission electrode 401 and the external metal plate.

Figure 7:
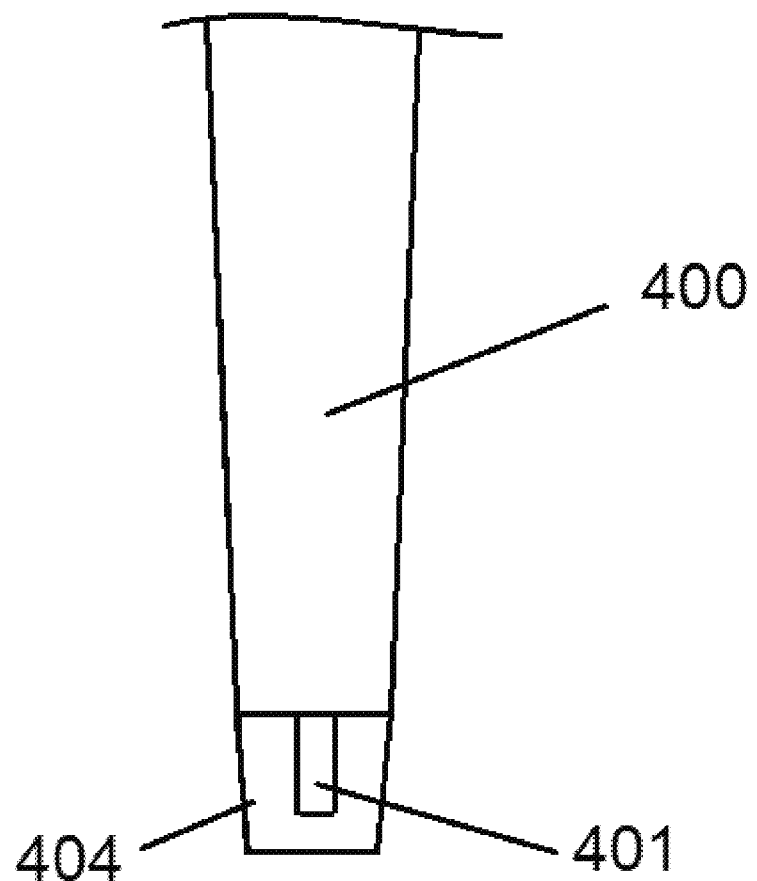
FIG. 7 is a cross-sectional view of components of the plasma emission part according to one embodiment.

In addition, as shown in FIG. 7, the plasma emission part 400 may further comprise a transparent member 404 at an end thereof. The transparent member 404 may be formed of a plastic-, acrylic-, resin-, ceramic-, or quartz-based material. By providing the transparent member 404, the user may easily grasp the emission state of the plasma flame.

Figure 8:
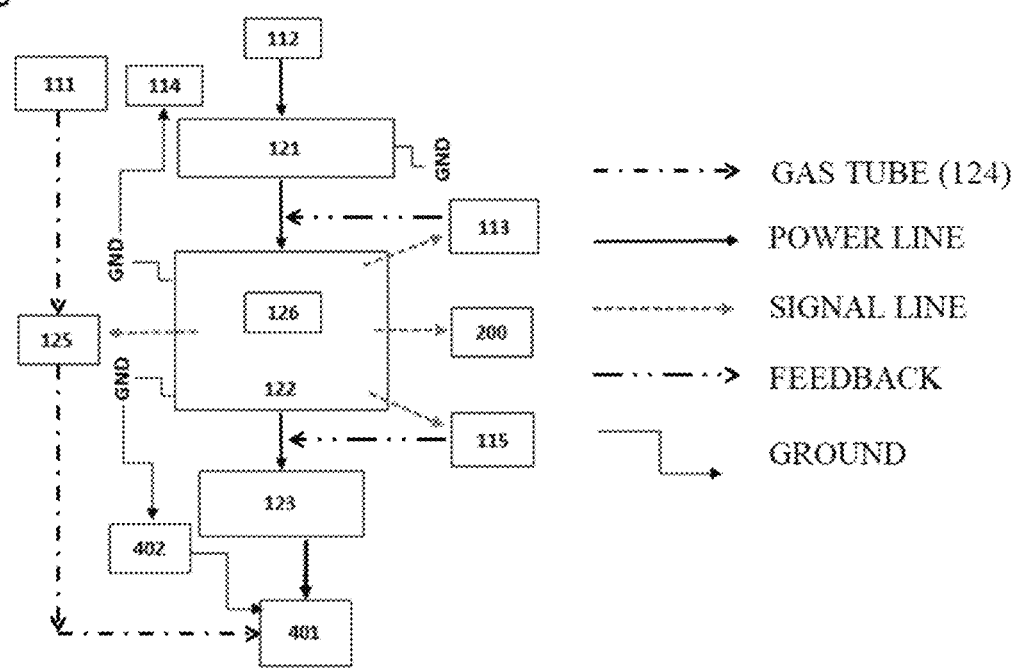
FIG. 8 illustrates a connection relationship of components of the portable plasma device according to the first embodiment.

FIG. 8 illustrates a connection relationship of each component of the portable plasma device of the present disclosure. The inner space of the housing 100 may comprise a battery 121, an oscillator 122, a transformer 123, a gas tube 124, a valve 125, and a control circuit 126.

The battery 121 is connected to the charging terminal 112 to be charged and discharged and may be attachable and detachable. The oscillator 122 acts as a generator and receives DC power from the battery and outputs AC power. The transformer 123 changes the level of the AC power output from the oscillator 122. The gas tube 124 is connected to the gas inlet 111 to deliver the gas introduced from the outside to the emission electrode 401. The valve 125 is connected to a portion of the gas tube 124 to control a movement of the gas by opening and closing operations. The control circuit 126 is connected in circuit with the power button 113, the external ground connection part 114, the setting button 115, the display part 116, the battery 121, the oscillator 122, the transformer 123, the valve 125, the emission electrode 401, the ground electrode 402, and the like to control the overall setting and operation of the plasma device, such as turning the plasma device on or off, setting the emission intensity of the plasma flame, opening and closing the valve 125, operating the emission electrode 401, setting the ground electrode 402, and operating the external ground connection part 114.

Meanwhile, the discharge of the emission electrode 401 may occur after a predetermined time elapses after the valve 125 is opened. When the emission electrode 401 is discharged with such a time difference, it is possible to prevent a plasma flame from being generated by reacting with nitrogen ($N_2$) in the atmosphere and to generate the desired kind of plasma flame using only the gas to be used purely. In addition, since the discharge is performed after the emission of the gas, unnecessary power consumption may be reduced, contaminants such as fine dust existing on a surface of a vial, a test tube, a well plate, or the like may be removed by the pressure of the emitted gas, and an initial emission intensity of the plasma flame may be controlled to a constant level. In a specific example, the time taken until the discharge is made after the opening may be adjusted through the settings of the control circuit 126.

According to the present disclosure, there can be provided a portable plasma device which is convenient to carry and has excellent performance and is capable of simply, uniformly, and locally treating an inner surface of a microstructure such as a microwell plate by easily adjusting a plasma flame.

The present embodiment and the drawings attached to the present specification clearly show only a part of technical ideas included in the above-described disclosure, and it will be apparent to those skilled in the art that various modifications and specific embodiments that those skilled in the art can easily devise are within the scope of the foregoing description of the technical scope of the present disclosure.

What is claimed is:

1. A portable plasma device comprising:
   a housing;
   a push member positioned on one surface of the housing and installed to be movable downward in a longitudinal direction of the housing to control emission of a plasma flame;
   a holding member provided on a surface opposite to one surface on which the push member is installed;
   a plasma emission part positioned on a lower portion of the housing;
   a gas inlet;
   a charging terminal;
   a power button;
   an external ground connection part;
   a setting button configured to set an output intensity of the plasma flame; and a display part configured to display a setting and operating state, wherein the plasma emission part is formed in an asymmetrical shape biased to one side with respect to a central axis of the housing in the longitudinal direction, wherein the plasma emission part comprises:
- an emission electrode configured to perform a plasma discharge;
- a ground electrode disposed to be spaced apart from the emission electrode so as to surround a periphery of the emission electrode; and
- a dielectric wall positioned between the emission electrode and the ground electrode, and wherein the dielectric wall is coated on at least one of the emission electrode and the ground electrode.

2. The portable plasma device of claim 1, wherein a transparent member is provided at an end of the plasma emission part to surround the end of the plasma emission part.

3. The portable plasma device of claim 2, wherein an inner space is formed inside the housing and wherein the inner space of the housing further comprises:
- a battery connected to the charging terminal to be charged and discharged;
- an oscillator configured to receive DC power from the battery and output AC power;
- a transformer configured to change a level of the AC power;
- a gas tube connected to the gas inlet;
- a valve connected to a portion of the gas tube to control a movement of gas by opening and closing operations; and
- a control circuit configured to control setting and operation of the plasma device.

4. The portable plasma device of claim 3, wherein, after the valve is opened, a discharge of the emission electrode is performed after a predetermined time elapses.

* * * * *